United States Patent
Chen

(10) Patent No.: US 11,911,497 B2
(45) Date of Patent: Feb. 27, 2024

(54) REBAUDIOSIDE E AND FOOD PRODUCTS SWEETENED WITH REBAUDIOSIDE E

(71) Applicant: Conagen Inc., Bedford, MA (US)

(72) Inventor: Steven Chen, Rancho Santa Margarita, CA (US)

(73) Assignee: Conagen Inc., Bedford, MA (US)

( * ) Notice: Subject to any disclaimer, the term of this patent is extended or adjusted under 35 U.S.C. 154(b) by 0 days.

(21) Appl. No.: 16/117,760

(22) Filed: Aug. 30, 2018

(65) Prior Publication Data

US 2019/0269162 A1    Sep. 5, 2019

Related U.S. Application Data

(63) Continuation of application No. 14/786,369, filed as application No. PCT/US2014/043255 on Jun. 19, 2014, now abandoned.

(60) Provisional application No. 61/837,097, filed on Jun. 19, 2013.

(51) Int. Cl.

| | |
|---|---|
| *A61K 8/60* | (2006.01) |
| *A23L 2/60* | (2006.01) |
| *A21D 13/062* | (2017.01) |
| *A23G 3/36* | (2006.01) |
| *A23G 4/06* | (2006.01) |
| *A21D 2/36* | (2006.01) |
| *A23G 3/38* | (2006.01) |
| *A23L 27/30* | (2016.01) |
| *A23L 27/00* | (2016.01) |
| *A23L 33/105* | (2016.01) |
| *A23L 33/125* | (2016.01) |
| *A23L 33/20* | (2016.01) |
| *A61K 47/26* | (2006.01) |
| *A61K 31/704* | (2006.01) |
| *A61Q 11/00* | (2006.01) |

(52) U.S. Cl.
CPC ............ *A61K 8/602* (2013.01); *A21D 2/36* (2013.01); *A21D 13/062* (2013.01); *A23G 3/36* (2013.01); *A23G 3/38* (2013.01); *A23G 4/06* (2013.01); *A23L 2/60* (2013.01); *A23L 27/36* (2016.08); *A23L 27/88* (2016.08); *A23L 33/105* (2016.08); *A23L 33/125* (2016.08); *A23L 33/20* (2016.08); *A61K 31/704* (2013.01); *A61K 47/26* (2013.01); *A61Q 11/00* (2013.01); *A23V 2002/00* (2013.01); *A61K 2800/10* (2013.01)

(58) Field of Classification Search
CPC ...... A61K 8/602; A61K 47/26; A61K 31/704; A61K 2800/10; A61Q 11/00; A21D 13/062; A21D 2/36; A23L 33/125; A23L 27/88; A23L 2/60; A23L 33/105; A23L 27/36; A23L 33/20; A23G 3/36; A23G 4/06; A23G 3/38; A23V 2002/00; A23V 2200/132; A23V 2200/3322; A23V 2250/262

See application file for complete search history.

(56) References Cited

U.S. PATENT DOCUMENTS

| | | | |
|---|---|---|---|
| 4,612,942 A | * | 9/1986 | Dobberstein ........... A23F 3/405 131/276 |
| 2008/0226794 A1 | | 9/2008 | Bell et al. |
| 2008/0292775 A1 | | 11/2008 | Prakash et al. |
| 2011/0091629 A1 | * | 4/2011 | Abelyan ............... A21D 13/062 426/548 |
| 2011/0160311 A1 | | 6/2011 | Prakash et al. |
| 2012/0282389 A1 | | 11/2012 | Purkayastha et al. |
| 2014/0171519 A1 | | 6/2014 | Prakash et al. |
| 2014/0272068 A1 | | 9/2014 | Prakash et al. |
| 2015/0050410 A1 | | 2/2015 | Luo et al. |
| 2016/0183574 A1 | | 6/2016 | Chen |

FOREIGN PATENT DOCUMENTS

| | | |
|---|---|---|
| CN | 102766667 | 11/2012 |
| WO | 2011112892 A1 | 9/2011 |
| WO | WO2012025828 A2 | 3/2012 |
| WO | 2012083251 A1 | 6/2012 |

OTHER PUBLICATIONS

Tanaka, Diversification of sweet substances—recent progress and development. Food Chemistry Series No. 8010. Techno Project Co, Ltd. Sep. 30-31, 1980. Japanese.
Third Party Submission dated Jun. 13, 2017 in corresponding Japanese Application No. JP 2016-521820.
Extended Search Report from EP 14814120.3, dated Dec. 7, 2016.
International Preliminary Report on Patentability from PCT/US2014/0432255, dated Dec. 30, 2015.
Priya et al., "Natural Sweeteners: A Complete Review," J. Pharm. Res.; vol. 4, No. 7, pp. 2034-2039 (2011).
PCT/US2014/043255, Oct. 15, 2014, International Search Report and Written Opinion.

* cited by examiner

*Primary Examiner* — Lezah Roberts
(74) *Attorney, Agent, or Firm* — Wolf, Greenfield & Sacks, P.C.

(57) ABSTRACT

The present disclosure is generally directed to orally consumable products, such as foodstuffs and beverages, containing rebaudioside E present in, e.g., about 5 ppm to about 100 ppm, and to methods for preparing such orally consumable products.

13 Claims, 1 Drawing Sheet

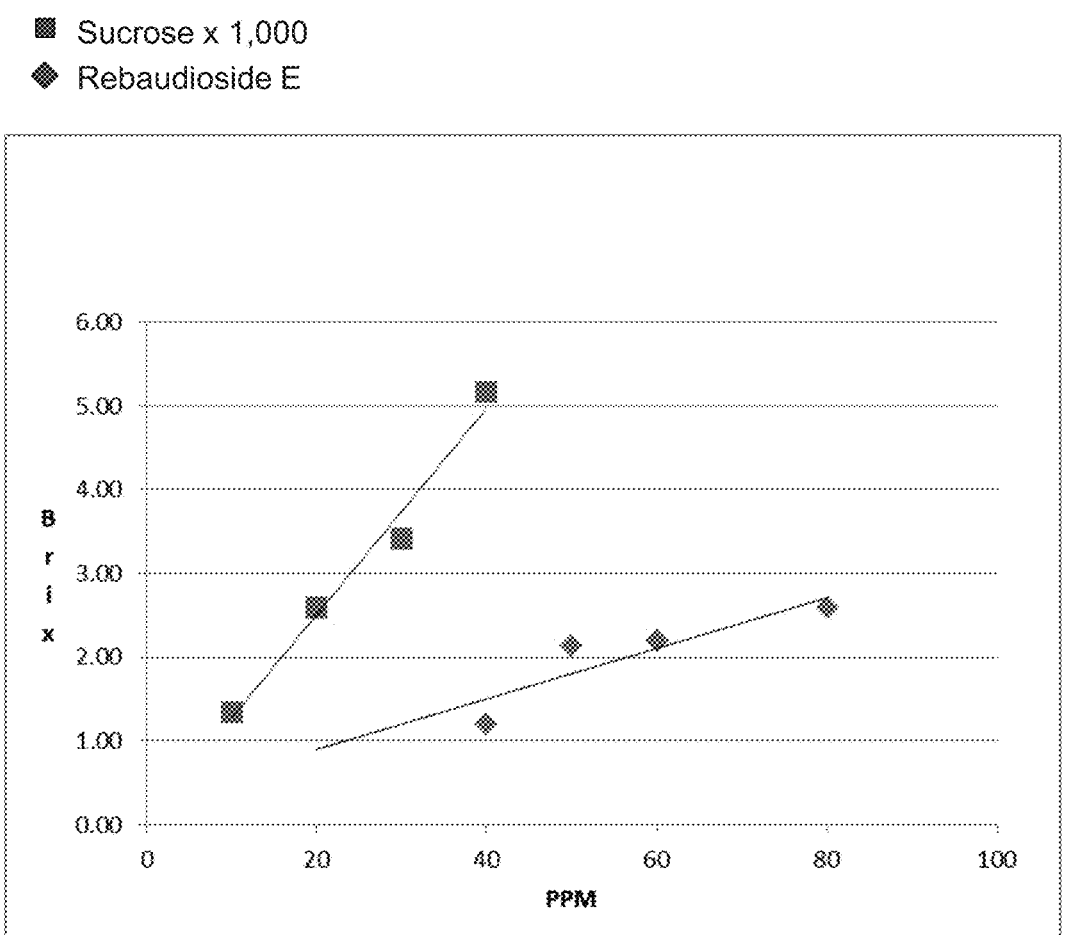

REBAUDIOSIDE E AND FOOD PRODUCTS SWEETENED WITH REBAUDIOSIDE E

CROSS-REFERENCE TO RELATED APPLICATIONS

This application is a continuation of U.S. patent application Ser. No. 14/786,369, filed Oct. 22, 2015, which claims the benefit of U.S. Provisional Patent Application No. 61/837,097, filed Jun. 19, 2013, the disclosures of both of which are hereby incorporated by reference in their entirety.

FIELD OF THE INVENTION

This invention relates to orally consumable products, such as foods and beverages containing rebaudioside E.

BACKGROUND OF THE INVENTION

There is a need for new food and beverage formulations that can adequately meet one or a combination of commercial objectives, such as nutritional characteristics, flavor, and/or shelf-life. Such food and beverage formulations are desirable to meet changing market demands. In particular, there is market demand for foods and beverages having alternative nutritional characteristics, including, for example, low/zero calorie content. Also, there is consumer interest in food and beverage formulations that are organic and/or all natural, or that make greater use of natural ingredients, such as ingredients distilled, extracted, concentrated, or similarly obtained from harvested plants or other naturally occurring sources, typically with limited or no further processing.

One problem with developing new food and beverage formulations employing alternative sweeteners is the associated bitterness and other off-tastes of such sweeteners. For example, it has been reported that, in addition to sweetness, certain steviol glycosides and other components of *Stevia* extract exhibit bitterness or other off-tastes.

Steviol glycosides include potent, non-nutritive sweet-tasting compounds that can be extracted as natural sweeteners from the *Stevia* plants, such as *Stevia rebaudiana*. Typically, these compounds are found to include stevioside (in an amount of 4-13% dry weight); steviolbioside (in trace amounts); rebaudiosides, including primarily rebaudioside A along with rebaudioside B, rebaudioside C, rebaudioside D, and rebaudioside E; and dulcosides, including dulcoside A (in an amount of 0.4-0.7% dry weight) and dulcoside B. Rebaudioside A has been shown to be present in *Stevia* plants at 4-7% (dry weight of leaves), and rebaudioside A sweeteners are sold commercially. Other rebaudiosides have been shown to be present in *Stevia* plants at low amounts, including trace amounts of rebaudioside B, 1-2% (dry weight) of rebaudioside C, trace amounts of rebaudioside D, and trace amounts of rebaudioside E.

While *Stevia* leaves generally contain only about 1.4 weight percent rebaudioside A (Reb A), purification techniques often are used to increase the amount of rebaudioside A in the sweetener to at least about 85 weight percent Reb A, with the balance being primarily residual amounts of the other steviol glycosides. Rebaudioside A sweeteners, such as Reb A purified from *Stevia* leaves or a *Stevia* extract processed to increase the relative amount of Reb A, have been widely commercialized in the food industry. Since receiving GRAS (Generally Recognized As Safe) status, an approval mechanism widely used in the food and beverage industry, Reb A sweeteners have become popular, naturally-occurring, potent sweeteners in foods and beverages. Rebaudioside A is approximately 200 times sweeter than sucrose. However, the sweetness of Reb A sweeteners is accompanied by problems of off-tastes in many food and beverage formulations, such as carbonated cola flavored beverages, including slow on-set of sweetness, bitter aftertaste, licorice taste, and lingering aftertaste. In particular, bitter off-tastes are believed to have reduced commercialization of beverages sweetened with Reb A sweeteners, such as diet carbonated soft drinks. For example, such off-tastes tend to be more perceptible in diet carbonated cola soft drinks sweetened with a Reb A sweetener than in other beverage formulations.

Accordingly, there is a need for new sweeteners having desirable taste and nutritional characteristics.

All references cited herein, including patent applications and publications, are hereby incorporated by reference in their entirety.

BRIEF SUMMARY OF THE INVENTION

The present disclosure is generally directed to orally consumable products, such as foodstuffs and beverages, containing isolated or extracted rebaudioside E and to methods for preparing such orally consumable products. In some embodiments, the rebaudioside E is present in the product at a concentration of about 5 ppm to about 100 ppm. In some embodiments, low concentrations of rebaudioside E, e.g., below 100 ppm, has an equivalent sweetness to sucrose solutions having concentrations between 10,000 and 30,000 ppm.

Accordingly, certain aspects of the present disclosure relate to an orally consumable product containing rebaudioside E present in about 5 ppm to about 100 ppm. In certain embodiments, the orally consumable product is selected from a foodstuff composition, a beverage product, a dietary supplement, a nutraceutical, an edible gel mix, an edible gel composition, a pharmaceutical composition, a dental composition, and an oral hygiene composition. In certain embodiments, the orally consumable product is a foodstuff composition selected from a confectionary composition, a condiment, a chewing gum, a cereal composition, a baked good, a dairy product, and a tabletop sweetener composition. In certain embodiments, the product is a carbonated or non-carbonated beverage product. In certain embodiments, the product is a beverage product selected from a soft drink, a fountain beverage, a frozen and ready-to-drink beverage, coffee, tea, a dairy beverage, a powdered soft drink, a liquid concentrate, flavored water, enhanced water, fruit juice, a fruit juice flavored drink, a sport drink, and an energy drink.

In certain embodiments that may be combined with any of the preceding embodiments, the rebaudioside E is the only sweetener, and the product has a sweetness intensity equivalent to about 1% to about 4% (w/v-%) sucrose solution. In certain embodiments that may be combined with any of the preceding embodiments, the orally consumable product further includes an additional sweetener, where the product has a sweetness intensity equivalent to about 1% to about 10% (w/v-%) sucrose solution. In certain embodiments that may be combined with any of the preceding embodiments, every sweetening ingredient in the product is a high intensity sweetener. In certain embodiments that may be combined with any of the preceding embodiments, every sweetening ingredient in the product is a natural high intensity sweetener. In certain embodiments that may be combined with any of the preceding embodiments, the additional sweetener contains one or more sweeteners selected from a *Stevia* extract, a steviol glycoside, stevioside, rebaudioside A, rebaudioside B, rebaudioside C, rebaudioside D, rebaudioside F, dulcoside A, rubusoside, steviolbioside, sucrose, high fructose corn syrup, fructose, glucose, xylose, arabinose, rhamnose, erythritol, xylitol, mannitol, sorbitol, inositol, AceK, aspartame, neotame, sucralose, saccharine, naringin dihydrochalcone (NarDHC), neohesperidin dihydrochalcone (NDHC), rubusoside, mogroside IV, siamenoside I, mogroside V, monatin, thaumatin, monellin, brazzein, L-alanine, glycine, Lo Han Guo, hernandulcin, phyllodulcin, trilobtain, and combinations thereof. In certain embodiments that may be combined with any of the preceding embodiments, the orally consumable product further includes one or more additives selected from a carbohydrate, a polyol, an amino acid or salt thereof, a poly-amino acid or salt thereof, a sugar acid or salt thereof, a nucleotide, an organic acid, an inorganic acid, an organic salt, an organic acid salt, an organic base salt, an inorganic salt, a bitter compound, a flavorant, a flavoring ingredient, an astringent compound, a protein, a protein hydrolysate, a surfactant, an emulsifier, a flavonoids, an alcohol, a polymer, and combinations thereof. In certain embodiments that may be combined with any of the preceding embodiments, the rebaudioside E has a purity of about 50% to about 100% by weight before it is added into the product. In certain embodiments that may be combined with any of the preceding embodiments, the rebaudioside E in the product is a rebaudioside E polymorph or amorphous rebaudioside E. In certain embodiments that may be combined with any of the preceding embodiments, the rebaudioside E in the product is a rebaudioside E stereoisomer.

Other aspects of the present disclosure relate to a method of preparing an orally consumable product by including purified rebaudioside E into the product or into the ingredients for making the product, where rebaudioside E is present in the product at a concentration of from about 5 ppm to about 100 ppm. Other aspects of the present disclosure relate to a method for enhancing the sweetness of an orally consumable product by adding from about 5 ppm to about 100 ppm of purified rebaudioside E into an orally consumable product, where the added rebaudioside E enhances the sweetness of the orally consumable product, as compared to a corresponding orally consumable product lacking the purified rebaudioside E.

In certain embodiments that may be combined with any of the preceding embodiments, the rebaudioside E is the only sweetener, and the product has a sweetness intensity equivalent to about 1% to about 4% (w/v-%) sucrose solution. In certain embodiments that may be combined with any of the preceding embodiments, the method further includes adding an additional sweetener, where the product has a sweetness intensity equivalent to about 1% to about 10% (w/v-%) sucrose solution.

Other aspects of the present disclosure relate to a method for preparing a sweetened orally consumable product, by: a) providing an orally consumable product containing one or more sweetener; and b) adding from about 5 ppm to about 100 ppm of purified rebaudioside E into the orally consumable product.

In certain embodiments that may be combined with any of the preceding embodiments, the method further includes adding one or more additives to the orally consumable product. In certain embodiments that may be combined with any of the preceding embodiments, the orally consumable product further contains one or more additives. In certain embodiments that may be combined with any of the preceding embodiments, the one or more additives are selected from a carbohydrate, a polyol, an amino acid or salt thereof, a poly-amino acid or salt thereof, a sugar acid or salt thereof, a nucleotide, an organic acid, an inorganic acid, an organic salt, an organic acid salt, an organic base salt, an inorganic salt, a bitter compound, a flavorant, a flavoring ingredient, an astringent compound, a protein, a protein hydrolysate, a surfactant, an emulsifier, a flavonoids, an alcohol, a polymer, and combinations thereof. In certain embodiments that may be combined with any of the preceding embodiments, every sweetening ingredient in the product is a high intensity sweetener. In certain embodiments that may be combined with any of the preceding embodiments, every sweetening ingredient in the product is a natural high intensity sweetener. In certain embodiments that may be combined with any of the preceding embodiments, the sweetener is selected from a *Stevia* extract, a steviol glycoside, stevioside, rebaudioside A, rebaudioside B, rebaudioside C, rebaudioside D, rebaudioside F, dulcoside A, rubusoside, steviolbioside, sucrose, high fructose corn syrup, fructose, glucose, xylose, arabinose, rhamnose, erythritol, xylitol, mannitol, sorbitol, inositol, AceK, aspartame, neotame, sucralose, saccharine, naringin dihydrochalcone (NarDHC), neohesperidin dihydrochalcone (NDHC), rubusoside, mogroside IV, siamenoside I, mogroside V, monatin, thaumatin, monellin, brazzein, L-alanine, glycine, Lo Han Guo, hernandulcin, phyllodulcin, trilobtain, and combinations thereof. In certain embodiments that may be combined with any of the preceding embodiments, the rebaudioside E has a purity of about 50% to about 100% by weight before it is added into the product. In certain embodiments that may be combined with any of the preceding embodiments, the rebaudioside E in the product is a rebaudioside E polymorph or amorphous rebaudioside E. In certain embodiments that may be combined with any of the preceding embodiments, the rebaudioside E in the product is a rebaudioside E stereoisomer.

BRIEF DESCRIPTION OF THE DRAWINGS

FIG. 1 shows the sweetness of rebaudioside E (Reb-E) and sucrose as function of concentration.

DETAILED DESCRIPTION OF THE INVENTION

Definitions

As used herein, the term "orally consumable product(s)" refers to an edible substances which are contacted with the mouth of man or animal, including substances that are taken into and subsequently ejected from the mouth and substances which are drunk, eaten, swallowed, or otherwise ingested; and that are safe for human or animal consumption when used in a generally acceptable range of concentrations.

As used herein, the term "stereoisomer" is a general term for all isomers of individual molecules that differ only in the orientation of their atoms in space. "Stereoisomer" includes enantiomers and isomers of compounds with more than one chiral center that are not mirror images of one another (diastereomers).

As used herein, the term "polymorphism" refers to the ability of a compound, such as rebaudioside E, to exist as two or more crystalline states that have different arrangements and/or conformations of the molecules in the crystal lattice. Polymorphism may cause physical properties such as density, melting point, and rate of dissolution to change. As used herein, a "rebaudioside E polymorph(s)" is a rebaudioside E molecule that has a different crystalline state having different arrangements and/or conformations of the molecules in the crystal lattice than the corresponding parent rebaudioside E molecule.

As used herein, the term "amorphous rebaudioside E" refers to a non-crystalline solid form of rebaudioside E.

As used herein, the term "sweetness intensity" refers to the relative strength of sweet sensation as observed or experienced by an individual, e.g., a human, or a degree or amount of sweetness detected by a taster, for example on a Brix scale.

As used herein, the term "enhancing the sweetness" refers to the effect of rebaudioside E in increasing, augmenting, intensifying, accentuating, magnifying, and/or potentiating the sensory perception of one or more sweetness characteristics of an orally consumable product of the present disclosure without changing the nature or quality thereof, as compared to a corresponding orally consumable product that does not contain rebaudioside E.

As used herein, the term "off-taste(s)" refers to an amount or degree of taste that is not characteristically or usually found in an orally consumable product of the present disclosure. For example, an off-taste is an undesirable taste of a sweetened consumable to consumers, such as, a bitter taste, a licorice-like taste, a metallic taste, an aversive taste, an astringent taste, a delayed sweetness onset, a lingering sweet aftertaste, and the like, etc.

As used herein, the term "carbohydrate sweetener" includes caloric sweeteners, such as, sucrose, fructose, glucose, high fructose corn syrup (containing fructose and glucose), xylose, arabinose, rhamnose, and sugar alcohols, such as erythritol, xylitol, mannitol, sorbitol, and inositol.

As used herein, the term "w/v-%" refers to the weight of a compound, such as a sugar, (in grams) for every 100 ml of a liquid orally consumable product of the present disclosure containing such compound.

As used herein, the term "w/w-%" refers to the weight of a compound, such as a sugar, (in grams) for every gram of an orally consumable product of the present disclosure containing such compound.

As used herein, the term "ppm" refers to part(s) per million by weight, for example, the weight of a compound, such as rebaudioside E (in milligrams) per kilogram of an orally consumable product of the present disclosure containing such compound (i.e., mg/kg) or the weight of a compound, such as rebaudioside E (in milligrams) per liter of an orally consumable product of the present disclosure containing such compound (i.e., mg/L); or by volume, for example the volume of a compound, such as rebaudioside E (in milliliters) per liter of an orally consumable product of the present disclosure containing such compound (i.e., ml/L).

As used herein, the term "flavor" refers to any food-grade material that may be added to or present in an orally consumable product of the present disclosure to provide a desired flavor.

As used herein, the singular form "a", "an", and "the" includes plural references unless indicated otherwise.

Reference to "about" a value or parameter herein refers to the usual error range for the respective value readily known to the skilled person in this technical field. Reference to "about" a value or parameter herein includes (and describes) aspects that are directed to that value or parameter per se. For example, description referring to "about X" includes description of "X."

Rebaudioside E

Certain aspects of the present disclosure relate to rebaudioside E and rebaudioside E-containing orally consumable products.

As disclosed herein, "rebaudioside E" and "Reb E" are used interchangeably and refer to the diterpene glycoside 13-[(2-O-β-D-glucopyranosyl-β-D-glucopyranosyl)oxy] ent-kaur-16-en-19-oic acid-(2-O-β-D-glucopyranosyl-β-D-glucopyranosyl) ester. The structure of rebaudioside E is depicted below:

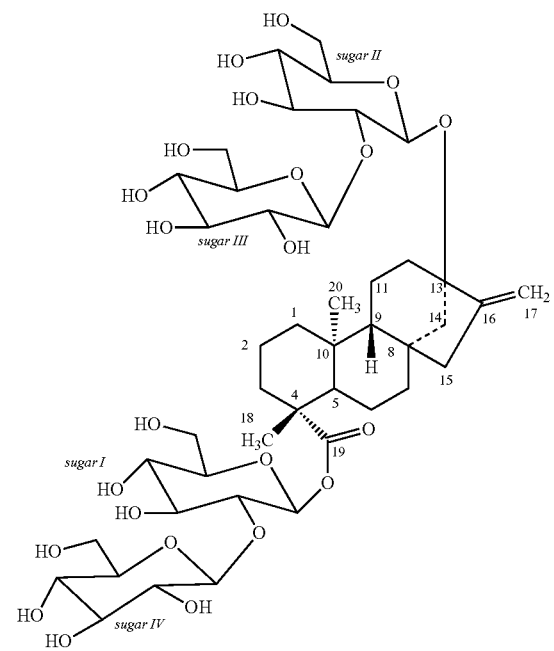

Diterpene glycosides, such as rebaudioside E, have been found in leaf extracts from the *Stevia* plant *Stevia rebaudiana* (Bertoni). Rebaudioside E has been found to be a minor component of *S. rebaudiana* that has a sweetness that is about 150 to 200 times greater than sucrose. Advantageously, rebaudioside E has zero calories and can be used wherever sugar (e.g., sucrose) is used.

In certain embodiments, rebaudioside E may also refer to a *Stevia* extract purified to increase the relative amount (concentration) of rebaudioside E.

Rebaudioside E may be obtained and/or isolated by extraction or the like from *Stevia* plants. *Stevia* (e.g., *Stevia rebaudiana* Bertoni) is a sweet-tasting plant. *Stevia* leaves contain a complex mixture of natural sweet diterpene glycosides, known as steviol glycosides, which are components of *Stevia* that contribute sweetness.

Any suitable technique known in the art for isolating and/or purifying compounds, such as rebaudiosides, from plants, such as *Stevia*, may be used. For example, rebaudioside E can be isolated and/or purified from *Stevia* plant material utilizing one or more of the techniques described in U.S. Pat. Nos. 3,723,410; 4,082,858; 4,361,697; 4,599,403; 5,112,610; 5,962,678; 8,299,224; 8,414,951; U.S. Patent Application Publication Nos. 2006/0083838; 2006/0134292; 2007/0082103; 2008/0300402; and Chaturvedula, V S P and Prakash, I, *Eur. Chem. Bull.* 2013, 2(5), 298-302. Alternatively, rebaudioside E can be chemically synthesized using methods well known to those of skill in the art.

In some embodiments, glycosides from leaves, such as rebaudioside E, can be extracted using either water or organic solvent extraction. Supercritical fluid extraction and steam distillation can also be used. In other embodiments, rebaudioside E can be recovered from *Stevia* plants using membrane technology. In some embodiments, production of an extract, such as a rebaudioside E extract, typically includes extraction of plant material with water or an water-organic solvent mixture, precipitation of high molecular weight substances, deionization and decolorization, purification on specific macroporous polymeric adsorbents, concentration, and drying.

In other embodiments, extracts of *Stevia* leaves may be purified to concentrate a selected component of the *Stevia* extract, such as rebaudioside E. For example, column chromatography may be used to isolate rebaudioside E from the other diterpene glycosides. In some embodiments, following chromatographic separation, rebaudioside E may optionally be recrystallized at least once, or at least twice, or at least three times, to obtain a *Stevia* extract containing a desired level of purity of rebaudioside E. In some embodiments, a *Stevia* extract used as the rebaudioside E component of an orally consumable product of the present disclosure has a purity of about 50% to about 100% by weight, about 55% to about 100% by weight, about 60% to about 100% by weight, about 65% to about 100% by weight, about 70% to about 100% by weight, about 75% to about 100% by weight, about 80% to about 100% by weight, about 85% to about 100% by weight, about 86% to about 100% by weight, about 87% to about 100% by weight, about 88% to about 100% by weight, about 89% to about 100% by weight, about 90% to about 100% by weight, about 91% to about 100% by weight, about 92% to about 100% by weight, about 93% to about 100% by weight, about 94% to about 100% by weight, about 95% to about 100% by weight, about 96% to about 100% by weight, about 97% to about 100% by weight, about 98% to about 100% by weight, or about 99% to about 100% by weight. Alternatively, a *Stevia* extract used as the rebaudioside E component of an orally consumable product of the present disclosure has a purity of about 50% to about 100% by weight, about 50% to about 99% by weight, about 50% to about 98% by weight, about 50% to about 97% by weight, about 50% to about 96% by weight, about 50% to about 95% by weight, about 50% to about 94% by weight, about 50% to about 93% by weight, about 50% to about 92% by weight, about 50% to about 91% by weight, about 50% to about 90% by weight, about 50% to about 85% by weight, about 50% to about 80% by weight, about 50% to about 75% by weight, about 50% to about 70% by weight, about 50% to about 65% by weight, about 50% to about 60% by weight, or about 50% to about 55% by weight. For example, a *Stevia* extract used as the rebaudioside E component of an orally consumable product of the present disclosure may have a purity of about 50%, about 55%, about 60%, about 65%, about 70%, about 75%, about 80%, about 85%, about 86%, about 87%, about 88%, about 89%, about 90%, about 91%, about 92%, about 93%, about 94%, about 95%, about 96%, about 97%, about 98%, about 99%, or about 100% by weight, including any range in between these values. In certain embodiments, a *Stevia* extract used as the rebaudioside E component of an orally consumable product of the present disclosure is substantially separated from other diterpene glycosides, including without limitation steviosides, steviolbiosides, other rebaudiosides (e.g., Reb A, Reb B, Reb C, Reb D, and Reb F), and dulcosides. As used herein, rebaudioside E is "substantially separated" from other diterpene glycosides in a *Stevia* extract when the extract is enriched in rebaudioside E by from about 50% to about 100%, including any values in between the range, as compared to the other diterpene glycosides.

In some embodiments, rebaudioside E is used in a purified and/or isolated form. In certain embodiments, rebaudioside E has less than 50%, less than 45%, less than 40%, less than 35%, less than 30%, less than 25%, less than 20%, less than 15%, less than 10%, less than 9%, less than 8%, less than 7%, less than 6%, less than 5%, less than 4%, less than 3%, less than 2%, or less than 1% of impurities other than water. Accordingly, in certain embodiments, the orally consumable products of the present disclosure will include rebaudioside E but no more than 50%, no more than 45%, no more than 40%, no more than 35%, no more than 30%, no more than 25%, no more than 20%, no more than 15%, no more than 10%, no more than 9%, no more than 8%, no more than 7%, no more than 6%, no more than 5%, no more than 4%, no more than 3%, no more than 2%, or no more than 1%, relative to rebaudioside E concentration, of other compounds isolated from *Stevia* plants, such as steviosides, steviolbiosides, other rebaudiosides (e.g., Reb A, Reb B, Reb C, Reb D, and Reb F), and dulcosides.

In some embodiments, the purified and/or isolated form of rebaudioside E has a purity of about 50% to about 100% by weight, about 55% to about 100% by weight, about 60% to about 100% by weight, about 65% to about 100% by weight, about 70% to about 100% by weight, about 75% to about 100% by weight, about 80% to about 100% by weight, about 85% to about 100% by weight, about 86% to about 100% by weight, about 87% to about 100% by weight, about 88% to about 100% by weight, about 89% to about 100% by weight, about 90% to about 100% by weight, about 91% to about 100% by weight, about 92% to about 100% by weight, about 93% to about 100% by weight, about 94% to about 100% by weight, about 95% to about 100% by weight, about 96% to about 100% by weight, about 97% to about 100% by weight, about 98% to about 100% by weight, or about 99% to about 100% by weight. Alternatively, the purified and/or isolated form of rebaudioside E has a purity of about 50% to about 100% by weight, about 50% to about 99% by weight, about 50% to about 98% by weight, about 50% to about 97% by weight, about 50% to about 96% by weight, about 50% to about 95% by weight, about 50% to about 94% by weight, about 50% to about 93% by weight, about 50% to about 92% by weight, about 50% to about 91% by weight, about 50% to about 90% by weight, about 50% to about 85% by weight, about 50% to about 80% by weight, about 50% to about 75% by weight, about 50% to about 70% by weight, about 50% to about 65% by weight, about 50% to about 60% by weight, or about 50% to about 55% by weight. For example, the purified and/or isolated form of rebaudioside E may have a purity of about 50%, about 55%, about 60%, about 65%, about 70%, about 75%, about 80%, about 85%, about 86%, about 87%, about 88%, about 89%, about 90%, about 91%, about 92%, about 93%, about 94%, about 95%, about 96%, about 97%, about 98%, about 99%, or about 100% by weight, including any range in between these values.

The purity of rebaudioside E extracted, isolated, and/or purified from *Stevia* plants can be assayed using any suitable method known in the art. For example, chromatography, such as HPLC, may be used to test the purity of rebaudioside E extracts.

In some embodiments, rebaudioside E of the present disclosure includes one or more rebaudioside E polymorphs and/or amorphous rebaudioside E. In other embodiments, rebaudioside E of the present disclosure includes a mixture of rebaudioside E polymorphs and/or amorphous rebaudioside E. In certain embodiments, rebaudioside E of the present disclosure includes one or more rebaudioside E stereoisomers. In other embodiments, rebaudioside E of the present disclosure includes a mixture of rebaudioside E stereoisomers.

Orally Consumable Products Containing Rebaudioside E

Other aspects of the present disclosure relate to orally consumable products containing rebaudioside E. In some embodiments, the rebaudioside E sweetens and/or enhances the sweetness of the orally consumable product.

In certain embodiments, rebaudioside E is present in orally consumable products of the present disclosure at a final concentration that ranges from about 5 ppm to about 100 ppm, from about 5 ppm to about 95 ppm, from about 5 ppm to about 90 ppm, from about 5 ppm to about 85 ppm, from about 5 ppm to about 80 ppm, from about 5 ppm to about 75 ppm, from about 5 ppm to about 70 ppm, from about 5 ppm to about 65 ppm, from about 5 ppm to about 60 ppm, from about 5 ppm to about 55 ppm, from about 5 ppm to about 50 ppm, from about 5 ppm to about 45 ppm, from about 5 ppm to about 40 ppm, from about 5 ppm to about 35 ppm, from about 5 ppm to about 30 ppm, from about 5 ppm to about 25 ppm, from about 5 ppm to about 20 ppm, from about 5 ppm to about 15 ppm, or from about 5 ppm to about 10 ppm. Alternatively, rebaudioside E is present in orally consumable products of the present disclosure at a final concentration that ranges from about 5 ppm to about 100 ppm, from about 10 ppm to about 100 ppm, from about 15 ppm to about 100 ppm, from about 20 ppm to about 100 ppm, from about 25 ppm to about 100 ppm, from about 30 ppm to about 100 ppm, from about 35 ppm to about 100 ppm, from about 40 ppm to about 100 ppm, from about 45 ppm to about 100 ppm, from about 50 ppm to about 100 ppm, from about 55 ppm to about 100 ppm, from about 60 ppm to about 100 ppm, from about 65 ppm to about 100 ppm, from about 70 ppm to about 100 ppm, from about 75 ppm to about 100 ppm, from about 80 ppm to about 100 ppm, from about 85 ppm to about 100 ppm, from about 90 ppm to about 100 ppm, or from about 95 ppm to about 100 ppm. For example, rebaudioside E may be present in orally consumable products of the present disclosure at a final concentration of about 5 ppm, about 10 ppm, about 15 ppm, about 20 ppm, about 25 ppm, about 30 ppm, about 35 ppm, about 40 ppm, about 45 ppm, about 50 ppm, about 55 ppm, about 60 ppm, about 65 ppm, about 70 ppm, about 75 ppm, about 80 ppm, about 85 ppm, about 90 ppm, about 95 ppm, or about 100 ppm, including any range in between these values. As used herein, "final concentration" refers to the concentration of, for example, rebaudioside E present in a final orally consumable product (i.e., after all ingredients and/or compounds have been added to produce the orally consumable product).

Accordingly, in certain embodiments, rebaudioside E has been added directly to a compound or ingredient from which the orally consumable product is made. The rebaudioside E may be present in a single compound or ingredient, or multiple compounds and ingredients. In other embodiments, rebaudioside E has been added directly to the orally consumable product. Any suitable method known in the art for adding a sweetener, such as rebaudioside E, may be used.

In some embodiments, the water solubility of rebaudioside E may be low. Accordingly, in certain embodiments, rebaudioside E can be provided as a supersaturated solution of rebaudioside E in an orally consumable product of the present disclosure. As used herein, the term "saturated" refers to the point of maximum concentration at which a solution of a substance (e.g., a rebaudioside E solution) can dissolve no more of that substance. The saturation point of a substance depends on the temperature of the liquid the substance is to be dissolved in, as well as the chemical nature of the liquid and the substance involved (e.g., the water and/or the rebaudioside E). As used herein, the term "supersaturated" refers to a solution that contains more of a dissolved material (e.g., rebaudioside E) than a saturated solution. Supersaturated solutions are typically achieved when one or more conditions of a saturated solution is changed, such as, e.g., temperature, volume (e.g., by evaporation), pressure, or the like.

In some embodiments, rebaudioside E in the orally consumable product has a purity of about 50% to about 100% by weight, about 55% to about 100% by weight, about 60% to about 100% by weight, about 65% to about 100% by weight, about 70% to about 100% by weight, about 75% to about 100% by weight, about 80% to about 100% by weight, about 85% to about 100% by weight, about 86% to about 100% by weight, about 87% to about 100% by weight, about 88% to about 100% by weight, about 89% to about 100% by weight, about 90% to about 100% by weight, about 91% to about 100% by weight, about 92% to about 100% by weight, about 93% to about 100% by weight, about 94% to about 100% by weight, about 95% to about 100% by weight, about 96% to about 100% by weight, about 97% to about 100% by weight, about 98% to about 100% by weight, or about 99% to about 100% by weight before it is added into the orally consumable product. Alternatively, rebaudioside E in the orally consumable product has a purity of about 50% to about 100% by weight, about 50% to about 99% by weight, about 50% to about 98% by weight, about 50% to about 97% by weight, about 50% to about 96% by weight, about 50% to about 95% by weight, about 50% to about 94% by weight, about 50% to about 93% by weight, about 50% to about 92% by weight, about 50% to about 91% by weight, about 50% to about 90% by weight, about 50% to about 85% by weight, about 50% to about 80% by weight, about 50% to about 75% by weight, about 50% to about 70% by weight, about 50% to about 65% by weight, about 50% to about 60% by weight, or about 50% to about 55% by weight before it is added into the orally consumable product. For example, rebaudioside E in the orally consumable product may have a purity of about 50%, about 55%, about 60%, about 65%, about 70%, about 75%, about 80%, about 85%, about 86%, about 87%, about 88%, about 89%, about 90%, about 91%, about 92%, about 93%, about 94%, about 95%, about 96%, about 97%, about 98%, about 99%, or about 100% by weight before it is added into the orally consumable product, including any range in between these values. In other embodiments, the rebaudioside E in the orally consumable product is substantially separated from other diterpene glycosides, including without limitation, steviosides, steviolbiosides, other rebaudiosides (e.g., Reb A, Reb B, Reb C, Reb D, and Reb F), and dulcosides.

In certain embodiments, rebaudioside E is the only sweetener in the orally consumable product. In such embodiments, the orally consumable product has a sweetness intensity equivalent to about 1% to about 4% (w/v-%) sucrose solution, about 1% to about 3% (w/v-%) sucrose solution, or about 1% to about 2% (w/v-%) sucrose solution. Alternatively, the orally consumable product has a sweetness intensity equivalent to about 1% to about 4% (w/v-%) sucrose solution, about 2% to about 4% (w/v-%) sucrose solution, about 3% to about 4% (w/v-%) sucrose solution, or about 4%. For example, the orally consumable product may have a sweetness intensity equivalent to about 1%, about 2%, about 3%, or about 4% (w/v-%) sucrose solution, including any range in between these values.

In other embodiments, about 5 ppm to about 100 ppm rebaudioside E present in orally consumable products of the present disclosure is sufficient for the rebaudioside E to provide from about 10% to about 100% of the total sweetening of the orally consumable product. As used herein, the term "total sweetening of the orally consumable product" includes the sweetness of the orally consumable product contributed by any and all sweetening ingredients, as determined by a sensory test panel. A "sweetening ingredient" as disclosed herein, is one that is itself sweet and which itself contributes sweetness in the orally consumable product perceptible to the sensory panel. In some embodiments, about 5 ppm to about 100 ppm rebaudioside E present in orally consumable products of the present disclosure is sufficient for the rebaudioside E to provide about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or about 100% of the total sweetening of the orally consumable product.

In some embodiments, an orally consumable product of the present disclosure has a sweetness intensity equivalent to about 1% to about 25% (w/v-%) sucrose solution. For example, the orally consumable product may have a sweetness intensity equivalent to about 1% to about 9% (w/v-%) sucrose solution, about 1% to about 8% (w/v-%) sucrose solution, about 1% to about 7% (w/v-%) sucrose solution, about 1% to about 6% (w/v-%) sucrose solution, about 1% to about 5% (w/v-%) sucrose solution, or about 1% to about 4% (w/v-%) sucrose solution, including any values between these ranges. In some embodiments, the orally consumable product may have a sweetness intensity equivalent to about 2% to about 10% (w/v-%) sucrose solution, about 3% to about 10% (w/v-%) sucrose solution, about 4% to about 10% (w/v-%) sucrose solution, about 5% to about 10% (w/v-%) sucrose solution, about 6% to about 10% (w/v-%) sucrose solution, or about 7% to about 10% (w/v-%) sucrose solution, including any values between these ranges. In some embodiments, the sweetness intensity may be equivalent to about 10% to about 11% (w/v-%) sucrose solution, about 10% to about 12% (w/v-%) sucrose solution, about 10% to about 13% (w/v-%) sucrose solution, about 10% to about 14% (w/v-%) sucrose solution, about 10% to about 15% (w/v-%) sucrose solution, about 10% to about 16% (w/v-%) sucrose solution, about 10% to about 17% (w/v-%) sucrose solution, about 10% to about 18% (w/v-%) sucrose solution, about 10% to about 19% (w/v-%) sucrose solution, about 10% to about 20% (w/v-%) sucrose solution, about 10% to about 21% (w/v-%) sucrose solution, about 10% to about 22% (w/v-%) sucrose solution, about 10% to about 23% (w/v-%) sucrose solution, about 10% to about 24% (w/v-%) sucrose solution, or about 10% to about 25% (w/v-%) sucrose solution, including any values between these ranges.

In some embodiments, orally consumable products contain one or more additional sweeteners. The one or more additional sweeteners may already be present in the orally consumable product or may be added to the orally consumable product, or one or more compounds or ingredients used to make the orally consumable product. In certain embodiments, the one or more additional sweeteners can include, without limitation, natural sweeteners, and artificial or synthetic sweeteners. Suitable sweeteners and combinations of sweeteners may be selected for the desired nutritional characteristics, taste profile, mouthfeel, and other organoleptic factors. In some embodiments, the one or more additional sweeteners include high intensity sweeteners and/or natural high intensity sweeteners, including, without limitation, *Stevia* extracts, steviol glycosides, steviosides, rebaudioside A, rebaudioside B, rebaudioside C, rebaudioside D, rebaudioside F, dulcoside A, rubusosides, steviolbiosides, sucrose, high fructose corn syrup, fructose, glucose, xylose, arabinose, rhamnose, erythritol, xylitol, mannitol, sorbitol, inositol, AceK, aspartame, neotame, sucralose, saccharine, naringin dihydrochalcone (NarDHC), neohesperidin dihydrochalcone (NDHC), rubusoside, mogroside IV, siamenoside I, mogroside V, monatin, thaumatin, monellin, brazzein, L-alanine, glycine, Lo Han Guo, hernandulcin, phyllodulcin, trilobtain, and combinations thereof. In some embodiments, caloric sweeteners, such as sucrose, are excluded from the orally consumable products.

In other embodiments, orally consumable products of the present disclosure can include a mixture of rebaudioside E and one or more sweeteners of the present disclosure in a ratio sufficient to achieve a desirable sweetness intensity, nutritional characteristic, taste profile, mouthfeel, or other organoleptic factor.

In some embodiments, orally consumable products of the present disclosure may contain one or more additives. The one or more additives may be present to add or enhance one or more characteristics of the orally consumable product, such as flavor, texture, aroma, color, shelf-life, etc. The one or more additives may already be present in the orally consumable product or may be added to the orally consumable product, or one or more compounds or ingredients used to make the orally consumable product. The orally consumable product may contain any suitable additive known in the art. Examples of suitable additives include, without limitation, carbohydrates, polyols, amino acids or salts thereof, poly-amino acids or salt thereof, sugar acids or salts thereof, nucleotides, organic acids, inorganic acids, organic salts, organic acid salts, organic base salts, inorganic salts, bitter compounds, flavorants, flavoring ingredients, astringent compounds, proteins, protein hydrolysates, surfactants, emulsifiers, flavonoids, alcohols, polymers, preservatives, thickening agents, food colorings, and combinations thereof.

Rebaudioside E can be present in any suitable orally consumable product known in the art. Examples of suitable orally consumable products include, without limitation, foodstuff compositions, beverage products, dietary supplements, nutraceuticals, edible gel mixes, edible gel compositions, pharmaceutical compositions, dental compositions, and oral hygiene compositions.

Foodstuff Compositions

In certain embodiments, from about 5 ppm to about 100 ppm of rebaudioside E is present in foodstuff compositions. As used herein, "foodstuff composition(s)" refers to any solid or liquid ingestible material that may, but need not, have a nutritional value and is intended for consumption by man or animal.

Examples of suitable foodstuff compositions include, without limitation, beverages (both carbonated and non-carbonated), such as coffee, teas, herbal teas, fruit drinks, and the like; confectionary compositions, such as candies, mints, fruit flavored drops, cocoa products, chocolates, and the like; condiments, such as ketchup, mustard, mayonnaise, and the like; chewing gums; cereal compositions; baked goods, such as breads, cakes, pies, cookies, and the like; dairy products, such as milk, cheese, cream, ice cream, sour cream, yoghurt, sherbet, and the like; tabletop sweetener compositions; soups; stews; convenience foods; meats, such as ham, bacon, sausages, jerky, and the like; gelatins and gelatin-like products such as jams, jellies, preserves, and the like; fruits; vegetables; egg products; icings; syrups including molasses; snacks; nut meats and nut products; and animal feed.

Foodstuff compositions may also include herbs, spices and seasonings, natural and synthetic flavors, and flavor enhancers, such as monosodium glutamate. In some embodiments, foodstuff compositions include, without limitation, prepared packaged products, such as dietetic sweeteners, liquid sweeteners, granulated flavor mixes which upon reconstitution with water provide non-carbonated drinks, instant pudding mixes, instant coffee and tea, coffee whiteners, malted milk mixes, pet foods, livestock feed, tobacco, and materials for baking applications, such as powdered baking mixes for the preparation of breads, cookies, cakes, pancakes, donuts and the like. In other embodiments, foodstuff compositions also include diet or low-calorie food and beverages containing little or no sucrose.

Beverage Products

In certain embodiments, from about 5 ppm to about 100 ppm of rebaudioside E is present in beverage products. Beverage products of the present disclosure include both carbonated and non-carbonated beverage products. Examples of suitable beverage products include, without limitation, soft drinks, fountain beverages, frozen beverages, ready-to-drink beverages, coffee, teas, dairy beverages, powdered soft drinks, liquid concentrates, flavored water, enhanced water, fruit juices, fruit juice flavored drinks, sport drinks, energy drinks, and alcoholic beverages, such as beers, wines, and liquors.

In some embodiments, a beverage product of the present disclosure includes one or more beverage ingredients including, without limitation, acidulants, fruit juices and/or vegetable juices, pulp, etc., flavorings, coloring, preservatives, vitamins, minerals, electrolytes, erythritol, tagatose, glycerine, and carbon dioxide. Such beverage products may be provided in any suitable form, such as a beverage concentrate or a carbonated, ready-to-drink beverage.

In certain embodiments, beverage products of the present disclosure may have any of numerous different specific formulations or constitutions. The formulation of a beverage product of the present disclosure may vary to a certain extent, depending upon such factors as the product's intended market segment, its desired nutritional characteristics, flavor profile, and the like. For example, in certain embodiments, it will generally be an option to add further ingredients to the formulation of a particular beverage product. For example, additional (i.e., more and/or other) sweeteners may be added, flavorings, electrolytes, vitamins, fruit juices or other fruit products, tastents, masking agents and the like, flavor enhancers, and/or carbonation typically may be added to any such formulations to vary the taste, mouthfeel, nutritional characteristics, etc. In embodiments, the beverage product is a cola beverage that contains water, about 5 ppm to about 100 ppm rebaudioside E, an acidulant, and flavoring. Exemplary flavorings include, without limitation, cola flavoring, citrus flavoring, and spice flavorings. In some embodiments, carbonation in the form of carbon dioxide may be added for effervescence. In other embodiments, preservatives may be added, depending upon the other ingredients, production technique, desired shelf life, etc. In certain embodiments, caffeine may be added. In some embodiments, the beverage product is a cola-flavored carbonated beverage, characteristically containing carbonated water, sweetener, kola nut extract and/or other flavoring, caramel coloring, one or more acids, and optionally other ingredients.

Acidulants that may be used with beverage products of the present disclosure may serve any one or more of several functions, including without limitation, lending tartness to the taste of the beverage product, enhancing palatability, increasing thirst quenching effect, modifying sweetness and acting as a mild preservative. Suitable acids are well known in the art and include, without limitation, phosphoric acid, citric acid, malic acid, tartaric acid, lactic acid, fumaric acid, ascorbic acid, gluconic acid, succinic acid, maleic acid, adipic acid, cinnamic acid, glutaric acid, and combinations thereof.

Dietary Supplements and Nutraceuticals

In certain embodiments, from about 5 ppm to about 100 ppm of rebaudioside E is present in dietary supplements. As used herein, "dietary supplement(s)" refers to compounds intended to supplement the diet and provide nutrients, such as vitamins, minerals, fiber, fatty acids, amino acids, etc. that may be missing or may not be consumed in sufficient quantities in a diet. Any suitable dietary supplement known in the art may be used. Examples of suitable dietary supplements include, without limitation, nutrients, vitamins, minerals, fiber, fatty acids, herbs, botanicals, amino acids, and metabolites.

In some embodiments, from about 10 ppm to about 100 ppm of rebaudioside E is present in nutraceuticals. As sued herein, "nutraceutical(s)" refers to compounds, which includes any food or part of a food that may provide medicinal or health benefits, including the prevention and/or treatment of disease or disorder (e.g., fatigue, insomnia, effects of aging, memory loss, mood disorders, cardiovascular disease and high levels of cholesterol in the blood, diabetes, osteoporosis, inflammation, autoimmune disorders, etc.). Any suitable nutraceutical known in the art may be used. In some embodiments, nutraceuticals can be used as supplements to food and beverages and as pharmaceutical formulations for enteral or parenteral applications which may be solid formulations, such as capsules or tablets, or liquid formulations, such as solutions or suspensions.

In some embodiments, dietary supplements and nutraceuticals may further contain protective hydrocolloids (such as gums, proteins, modified starches), binders, film-forming agents, encapsulating agents/materials, wall/shell materials, matrix compounds, coatings, emulsifiers, surface active agents, solubilizing agents (oils, fats, waxes, lecithins, etc.), adsorbents, carriers, fillers, co-compounds, dispersing agents, wetting agents, processing aids (solvents), flowing agents, taste-masking agents, weighting agents, jellifying agents, gel-forming agents, antioxidants and antimicrobials.

Edible Gel Mixes and Gel Compositions

In certain embodiments, from about 5 ppm to about 100 ppm of rebaudioside E is present in gel mixes and gel compositions. As used herein, a "gel" refers to a colloidal system in which a network of particles spans the volume of a liquid medium. Although gels mainly are composed of liquids, and thus exhibit densities similar to liquids, gels have the structural coherence of solids due to the network of particles that spans the liquid medium. For this reason, gels generally appear to be solid, jelly-like materials. Gels can be used in a number of applications. For example, gels can be used in foods, paints, and adhesives. Gels that can be eaten are referred to as "edible gel compositions." Edible gel compositions typically are eaten as snacks, as desserts, as a part of staple foods, or along with staple foods. Examples of suitable edible gel compositions include, without limitation, gel desserts, puddings, jams, jellies, pastes, trifles, aspics, marshmallows, gummy candies, and the like. In some embodiments, edible gel mixes generally are powdered or granular solids to which a fluid may be added to form an edible gel composition. Examples of suitable fluids include, without limitation, water, dairy fluids, dairy analogue fluids, juices, alcohol, alcoholic beverages, and combinations thereof. Examples of suitable dairy fluids include, without limitation, milk, cultured milk, cream, fluid whey, and mixtures thereof. Examples of suitable dairy analogue fluids include, without limitation, soy milk and non-dairy coffee whitener.

As used herein, the term "gelling ingredient" refers to any material that can form a colloidal system within a liquid medium. Examples of suitable gelling ingredients include, without limitation, gelatin, alginate, carageenan, gum, pectin, konjac, agar, food acid, rennet, starch, starch derivatives, and combinations thereof. It is well known to those having ordinary skill in the art that the amount of gelling ingredient used in an edible gel mix or an edible gel composition varies considerably depending on a number of factors, including without limitation, the particular gelling ingredient used, the particular fluid base used, and the desired properties of the gel.

Gel mixes and gel compositions of the present disclosure may be prepared by any suitable method known in the art. In some embodiments, edible gel mixes and edible gel compositions of the present disclosure may be prepared using other ingredients in addition to rebaudioside E and the gelling agent. Examples of other suitable ingredients include, without limitation, a food acid, a salt of a food acid, a buffering system, a bulking agent, a sequestrant, a cross-linking agent, one or more flavors, one or more colors, and combinations thereof.

Pharmaceutical Compositions

In certain embodiments, from about 5 ppm to about 100 ppm of rebaudioside E is present in pharmaceutical compositions. Any suitable pharmaceutical composition known in the art may be used. In certain embodiments, a pharmaceutical composition of the present disclosure contains from about 5 ppm to about 100 ppm of rebaudioside E, and one or more pharmaceutically acceptable excipients. In some embodiments, pharmaceutical compositions of the present disclosure may be used to formulate pharmaceutical drugs containing one or more active agents that exert a biological effect. Accordingly, in some embodiments, pharmaceutical compositions of the present disclosure may contain one or more active agents that exert a biological effect. Suitable active agents are well known in the art (e.g., The Physician's Desk Reference). Such compositions can be prepared according to procedures well known in the art, for example, as described in Remington's Pharmaceutical Sciences, Mack Publishing Co., Easton, Pa., USA.

Examples of suitable active agents include, without limitation, bronchodilators, anorexiants, antihistamines, nutritional supplements, laxatives, analgesics, anesthetics, antacids, H.sub.2-receptor antagonists, anticholinergics, antidiarrheals, demulcents, antitussives, antinauseants, antimicrobials, antibacterials, antifungals, antivirals, expectorants, anti-inflammatory agents, antipyretics, and mixtures thereof. In one embodiment, the active agent is selected from the group consisting of antipyretics and analgesics, e.g., ibuprofen, acetaminophen, or aspirin; laxatives, e.g., phenolphthalein dioctyl sodium sulfosuccinate; appetite depressants, e.g., amphetamines, phenylpropanolamine, phenylpropanolamine hydrochloride, or caffeine; antacidics, e.g., calcium carbonate; antiasthmatics, e.g., theophylline; antidiuretics, e.g., diphenoxylate hydrochloride; agents active against flatulence, e.g., simethecon; migraine agents, e.g., ergotaminetartrate; psychopharmacological agents, e.g., haloperidol; spasmolytics or sedatives, e.g., phenobarbitol; antihyperkinetics, e.g., methyldopa or methylphenidate; tranquilizers, e.g., benzodiazepines, hydroxinmeprobramates or phenothiazines; antihistaminics, e.g., astemizol, chloropheniramine maleate, pyridamine maleate, doxlamine succinate, bromopheniramine maleate, phenyltoloxamine citrate, chlorocyclizine hydrochloride, pheniramine maleate, and phenindamine tartrate; decongestants, e.g., phenylpropanolamine hydrochloride, phenylephrine hydrochloride, pseudoephedrine hydrochloride, pseudoephedrine sulfate, phenylpropanolamine bitartrate, and ephedrine; beta-receptor blockers, e.g., propanolol; agents for alcohol withdrawal, e.g., disulfiram; antitussives, e.g., benzocaine, dextromethorphan, dextromethorphan hydrobromide, noscapine, carbetapentane citrate, and chlophedianol hydrochloride; fluorine supplements, e.g., sodium fluoride; local antibiotics, e.g., tetracycline or cleocine; corticosteroid supplements, e.g., prednisone or prednisolone; agents against goiter formation, e.g., colchicine or allopurinol; antiepileptics, e.g., phenytoine sodium; agents against dehydration, e.g., electrolyte supplements; antiseptics, e.g., cetylpyridinium chloride; NSAIDs, e.g., acetaminophen, ibuprofen, naproxen, or salts thereof; gastrointestinal active agents, e.g., loperamide and famotidine; various alkaloids, e.g., codeine phosphate, codeine sulfate, or morphine; supplements for trace elements, e.g., sodium chloride, zinc chloride, calcium carbonate, magnesium oxide, and other alkali metal salts and alkali earth metal salts; vitamins; ion-exchange resins, e.g., cholestyramine; cholesterol-depressant and lipid-lowering substances; antiarrhythmics, e.g., N-acetylprocainamide; and expectorants, e.g., guaifenesin. Suitable active substances which have a particularly unpleasant taste include, without limitation, antibacterial agents such as ciprofloxacin, ofloxacin, and pefloxacin; antiepileptics such as zonisamide; macrolide antibiotics such as erythromycin; beta-lactam antibiotics such as penicillins and cephalosporins; psychotropic active substances such as chlorpromazine; active substances such as sulpyrine; and agents active against ulcers, such as cimetidine. In another embodiment, the pharmaceutical composition of the present invention comprises at least one amino acid selected from the group consisting of glycine, L-alanine, L-arginine, L-aspartic acid, L-cystine, L-glutamic acid, L-glutamine, L-histidine, L-isoleucine, L-leucine, L-lysine, L-methionine, L-ornithine, L-phenylalanine, L-proline, L-serine, L-threonine, L-tryptophan, L-tyrosine, L-valine, creatine, and mixtures thereof.

In some embodiments, pharmaceutical compositions of the present disclosure can be administered to a subject in any form suitable to achieve their intended purpose. In certain preferred embodiments, the composition is one which can be administered buccally or orally. Alternatively, the pharmaceutical composition may be an oral or nasal spray. Suitable subjects include, without limitation, any animal, such as a human. Other suitable animals include, without limitation, canines, felines, dogs, cats, livestock, horses, cattle, sheep, and the like. A veterinary composition, as used herein, refers to a pharmaceutical composition that suitable for non-human animals. Such veterinary compositions are well known in the art.

In some embodiments, a pharmaceutical composition of the present disclosure is a liquid dosage form for oral administration, including, without limitation, pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

In other embodiments, pharmaceutical compositions of the present disclosure can be in the form of chewable tablets (e.g., U.S. Pat. Nos. 4,684,534 and 6,060,078); orally disintegrating compositions (e.g., U.S. Pat. Nos. 6,368,625 and 6,316,029); nasal compositions (e.g., U.S. Pat. No. 6,187,332); solid dosage forms, such as water and/or saliva activated effervescent granule (e.g., U.S. Pat. No. 6,649,186); film-shaped or wafer-shaped pharmaceutical compositions; gum base formulations having a medicament or agent and rebaudioside E contained in a coating that surrounds the gum base formulation (e.g., U.S. Pat. No. 6,773,716); and aerosols (e.g., U.S. Pat. No. 5,011,678).

Dental and Oral Hygiene Compositions

In certain embodiments, from about 5 ppm to about 100 ppm of rebaudioside E is present in dental and oral hygiene compositions. Any suitable dental and oral hygiene compositions known in the art may be used. Examples of suitable dental and oral hygiene compositions include, without limitation, toothpastes, tooth polishes, dental floss, mouthwashes, mouthrinses, dentrifices, mouth sprays, mouth refreshers, plaque rinses, dental pain relievers, and the like.

Methods of Producing Orally Consumable Products Containing Rebaudioside E

Other aspects of the present disclosure relate to methods of preparing and/or enhancing the sweetness of orally consumable products of the present disclosure containing rebaudioside E. Examples of suitable orally consumable products that may be prepared by the methods of the present disclosure include, without limitation, any of the foodstuff compositions, beverage products, dietary supplements, nutraceuticals, edible gel mixes, edible gel compositions, pharmaceutical compositions, dental compositions, and oral hygiene compositions disclosed herein. In some embodiments, rebaudioside E is included and/or added directly to the orally consumable product, or included and/or added to a compound or ingredient from which the orally consumable product is made. In other embodiments, the rebaudioside E to be included and/or added to the orally consumable product is a rebaudioside E polymorph, amorphous rebaudioside E, or a rebaudioside E stereoisomer.

In certain embodiments, rebaudioside E is included and/or added at a final concentration that is sufficient to sweeten and/or enhance the sweetness of the orally consumable product. The "final concentration" of rebaudioside E refers to the concentration of rebaudioside E present in the final orally consumable product (i.e., after all ingredients and/or compounds have been added to produce the orally consumable product). Accordingly, in certain embodiments, rebaudioside E is included and/or added to a compound or ingredient used to prepare the orally consumable product. The rebaudioside E may be present in a single compound or ingredient, or multiple compounds and ingredients. In other embodiments, rebaudioside E is included and/or added to the orally consumable product. In certain preferred embodiments, the rebaudioside E is included and/or added at a final concentration that ranges from about 5 ppm to about 100 ppm, from about 5 ppm to about 95 ppm, from about 5 ppm to about 90 ppm, from about 5 ppm to about 85 ppm, from about 5 ppm to about 80 ppm, from about 5 ppm to about 75 ppm, from about 5 ppm to about 70 ppm, from about 5 ppm to about 65 ppm, from about 5 ppm to about 60 ppm, from about 5 ppm to about 55 ppm, from about 5 ppm to about 50 ppm, from about 5 ppm to about 45 ppm, from about 5 ppm to about 40 ppm, from about 5 ppm to about 35 ppm, from about 5 ppm to about 30 ppm, from about 5 ppm to about 25 ppm, from about 5 ppm to about 20 ppm, from about 5 ppm to about 15 ppm, or from about 5 ppm to about 10 ppm. Alternatively, the rebaudioside E is included and/or added at a final concentration that ranges from about 5 ppm to about 100 ppm, from about 10 ppm to about 100 ppm, from about 15 ppm to about 100 ppm, from about 20 ppm to about 100 ppm, from about 25 ppm to about 100 ppm, from about 30 ppm to about 100 ppm, from about 35 ppm to about 100 ppm, from about 40 ppm to about 100 ppm, from about 45 ppm to about 100 ppm, from about 50 ppm to about 100 ppm, from about 55 ppm to about 100 ppm, from about 60 ppm to about 100 ppm, from about 65 ppm to about 100 ppm, from about 70 ppm to about 100 ppm, from about 75 ppm to about 100 ppm, from about 80 ppm to about 100 ppm, from about 85 ppm to about 100 ppm, from about 90 ppm to about 100 ppm, or from about 95 ppm to about 100 ppm. For example, rebaudioside E may be included and/or added at a final concentration of about 5 ppm, about 10 ppm, about 15 ppm, about 20 ppm, about 25 ppm, about 30 ppm, about 35 ppm, about 40 ppm, about 45 ppm, about 50 ppm, about 55 ppm, about 60 ppm, about 65 ppm, about 70 ppm, about 75 ppm, about 80 ppm, about 85 ppm, about 90 ppm, about 95 ppm, or about 100 ppm, including any range in between these values.

In some embodiments, the rebaudioside E that is included and/or added to the orally consumable product has a purity of about 50% to about 100% by weight, about 55% to about 100% by weight, about 60% to about 100% by weight, about 65% to about 100% by weight, about 70% to about 100% by weight, about 75% to about 100% by weight, about 80% to about 100% by weight, about 85% to about 100% by weight, about 86% to about 100% by weight, about 87% to about 100% by weight, about 88% to about 100% by weight, about 89% to about 100% by weight, about 90% to about 100% by weight, about 91% to about 100% by weight, about 92% to about 100% by weight, about 93% to about 100% by weight, about 94% to about 100% by weight, about 95% to about 100% by weight, about 96% to about 100% by weight, about 97% to about 100% by weight, about 98% to about 100% by weight, or about 99% to about 100% by weight before it is added into the orally consumable product. Alternatively, the rebaudioside E that is included and/or added to the orally consumable product has a purity of about 50% to about 100% by weight, about 50% to about 99% by weight, about 50% to about 98% by weight, about 50% to about 97% by weight, about 50% to about 96% by weight, about 50% to about 95% by weight, about 50% to about 94% by weight, about 50% to about 93% by weight, about 50% to about 92% by weight, about 50% to about 91% by weight, about 50% to about 90% by weight, about 50% to about 85% by weight, about 50% to about 80% by weight, about 50% to about 75% by weight, about 50% to about 70% by weight, about 50% to about 65% by weight, about 50% to about 60% by weight, or about 50% to about 55% by weight before it is added into the orally consumable product. For example, the rebaudioside E that is included and/or added to the orally consumable product may have a purity of about 50%, about 55%, about 60%, about 65%, about 70%, about 75%, about 80%, about 85%, about 86%, about 87%, about 88%, about 89%, about 90%, about 91%, about 92%, about 93%, about 94%, about 95%, about 96%, about 97%, about 98%, about 99%, or about 100% by weight before it is added into the orally consumable product, including any range in between these values. In other embodiments, the rebaudioside E that is included and/or added to the orally consumable product is substantially separated from other diterpene glycosides, including without limitation, steviosides, steviolbiosides, other rebaudiosides (e.g., Reb A, Reb B, Reb C, Reb D, and Reb F), and dulcosides. As used herein, rebaudioside E is "substantially separated" from other diterpene glycosides when the rebaudioside E is enriched in rebaudioside E by from about 50% to about 100%, including any values in between the range, as compared to the other diterpene glycosides.

In certain embodiments, rebaudioside E is the only sweetener included and/or added to the orally consumable product. In such embodiments, the orally consumable product has a sweetness intensity equivalent to about 1% to about 4% (w/v-%) sucrose solution, about 1% to about 3% (w/v-%) sucrose solution, or about 1% to about 2% (w/v-%) sucrose solution. Alternatively, the orally consumable product has a sweetness intensity equivalent to about 1% to about 4% (w/v-%) sucrose solution, about 2% to about 4% (w/v-%) sucrose solution, about 3% to about 4% (w/v-%) sucrose solution, or about 4%. For example, the orally consumable product may have a sweetness intensity equivalent to about 1%, about 2%, about 3%, or about 4% (w/v-%) sucrose solution, including any range in between these values.

In other embodiments, including and/or adding about 5 ppm to about 100 ppm rebaudioside E in orally consumable products of the present disclosure is sufficient for the rebaudioside E to provide from about 10% to about 100% of the total sweetening of the orally consumable product. In some embodiments, including and/or adding about 5 ppm to about 100 ppm rebaudioside E present in orally consumable products of the present disclosure is sufficient for the rebaudioside E to provide about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or about 100% of the total sweetening of the orally consumable product.

In some embodiments, an orally consumable product of the present disclosure to which rebaudioside E is included and/or added has a sweetness intensity equivalent to about 1% to about 25% (w/v-%) sucrose solution. In such embodiments, the orally consumable product of the present disclosure to which rebaudioside E is included and/or added already contains one or more sweeteners. Alternatively, rebaudioside E and one or more additional sweeteners are added to an orally consumable product of the present disclosure to produce an orally consumable product of the present disclosure having a sweetness intensity equivalent to about 1% to about 25% (w/v-%) sucrose solution. In some embodiments, an orally consumable product of the present disclosure has a sweetness intensity equivalent to about 1% to about 10% (w/v-%) sucrose solution. For example, the orally consumable product may have a sweetness intensity equivalent to about 1% to about 9% (w/v-%) sucrose solution, about 1% to about 8% (w/v-%) sucrose solution, about 1% to about 7% (w/v-%) sucrose solution, about 1% to about 6% (w/v-%) sucrose solution, about 1% to about 5% (w/v-%) sucrose solution, or about 1% to about 4% (w/v-%) sucrose solution, including any values between these ranges. In some embodiments, the orally consumable product may have a sweetness intensity equivalent to about 2% to about 10% (w/v-%) sucrose solution, about 3% to about 10% (w/v-%) sucrose solution, about 4% to about 10% (w/v-%) sucrose solution, about 5% to about 10% (w/v-%) sucrose solution, about 6% to about 10% (w/v-%) sucrose solution, or about 7% to about 10% (w/v-%) sucrose solution, including any values between these ranges. In some embodiments, the sweetness intensity may be equivalent to about 10% to about 11% (w/v-%) sucrose solution, about 10% to about 12% (w/v-%) sucrose solution, about 10% to about 13% (w/v-%) sucrose solution, about 10% to about 14% (w/v-%) sucrose solution, about 10% to about 15% (w/v-%) sucrose solution, about 10% to about 16% (w/v-%) sucrose solution, about 10% to about 17% (w/v-%) sucrose solution, about 10% to about 18% (w/v-%) sucrose solution, about 10% to about 19% (w/v-%) sucrose solution, about 10% to about 20% (w/v-%) sucrose solution, about 10% to about 21% (w/v-%) sucrose solution, about 10% to about 22% (w/v-%) sucrose solution, about 10% to about 23% (w/v-%) sucrose solution, about 10% to about 24% (w/v-%) sucrose solution, or about 10% to about 25% (w/v-%) sucrose solution, including any values between these ranges.

In certain embodiments, the sweeteners can include, without limitation, natural sweeteners, and artificial or synthetic sweeteners. Suitable sweeteners and combinations of sweeteners may be selected for the desired nutritional characteristics, taste profile, mouthfeel, and other organoleptic factors. In some embodiments, the sweeteners include high intensity sweeteners and/or natural high intensity sweeteners, including, without limitation, *Stevia* extracts, steviol glycosides, steviosides, rebaudioside A, rebaudioside B, rebaudioside C, rebaudioside D, rebaudioside F, dulcoside A, rubusosides, steviolbiosides, sucrose, high fructose corn syrup, fructose, glucose, xylose, arabinose, rhamnose, erythritol, xylitol, mannitol, sorbitol, inositol, AceK, aspartame, neotame, sucralose, saccharine, naringin dihydrochalcone (NarDHC), neohesperidin dihydrochalcone (NDHC), rubusoside, mogroside IV, siamenoside I, mogroside V, monatin, thaumatin, monellin, brazzein, L-alanine, glycine, Lo Han Guo, hernandulcin, phyllodulcin, trilobtain, and combinations thereof. In some embodiments, caloric sweeteners, such as sucrose, are excluded from the orally consumable products.

In some embodiments, the orally consumable product produced by the methods of the present disclosure may contain one or more additives. The one or more additives may be present to add or enhance one or more characteristics of the orally consumable product, such as flavor, texture, aroma, color, shelf-life, etc. In some embodiments the orally consumable product to which rebaudioside E is included and/or added already contains the one or more additives. Alternatively, the one or more additives are added to the orally consumable product as a step in the methods of the present disclosure. The orally consumable product may contain any suitable additive known in the art. Examples of suitable additives include, without limitation, carbohydrates, polyols, amino acids or salts thereof, poly-amino acids or salt thereof, sugar acids or salts thereof, nucleotides, organic acids, inorganic acids, organic salts, organic acid salts, organic base salts, inorganic salts, bitter compounds, flavorants, flavoring ingredients, astringent compounds, proteins, protein hydrolysates, surfactants, emulsifiers, flavonoids, alcohols, polymers, preservatives, thickening agents, food colorings, and combinations thereof.

Accordingly in certain embodiments, the present disclosure provides methods of preparing an orally consumable product of the present disclosure by including purified rebaudioside E into the orally consumable product or into the ingredients for making the orally consumable product, where rebaudioside E is present in the orally consumable product at a concentration of from about 5 ppm to about 100 ppm.

In other embodiments, the present disclosure provides methods for enhancing the sweetness of an orally consumable product by adding from about 5 ppm to about 100 ppm of purified rebaudioside E into an orally consumable product of the present disclosure, where the added rebaudioside E enhances the sweetness of the orally consumable product, as compared to a corresponding orally consumable product lacking the purified rebaudioside E.

In other embodiments, the present disclosure provides methods for preparing a sweetened orally consumable product by: a) providing an orally consumable product of the present disclosure that contains one or more sweetener; and b) adding from about 5 ppm to about 100 ppm of purified rebaudioside E into the orally consumable product.

The invention will be more fully understood by reference to the following Examples. They should not, however, be construed as limiting the scope of the invention. All citations throughout the disclosure are hereby expressly incorporated by reference.

EXAMPLES

Example 1: Comparative Analysis Between High-Purity Rebaudioside E and Table Sugar The following Examples demonstrate the concentrations at which rebaudioside E (Reb-E) has an equivalent sweetness to table sugar.

Materials and Methods

Rebaudioside E (Reb-E) was produced to emulate the sweetness of table sugar (sucrose).

A standard sweetness test method was employed. Briefly, training sample solutions made of sucrose in water at 1-5% concentration (Brix) at 1% increments were prepared. Reb-E test samples were made of Reb-E in water at 20-60 ppm (parts per million). Panelists were trained to recognize and differentiate between each training solution. Three test solutions of known sucrose concentrations were given to panelists to ensure equal training and to establish a baseline.

Table 1 shows the training and test solutions.

TABLE 1

| Sucrose + 0.6% citric acid | Reb-E + 0.6% citric Acid |
|---|---|
| 1% (10 × 1,000 PPM) | 20 PPM |
| 2% (20 × 1,000 PPM) | 40 PPM |
| 3% (30 × 1,000 PPM) | 50 PPM |
| 4% (40 × 1,000 PPM) | 60 PPM |

Test solutions were randomized using a random number generator. Two sets of tests were generated for each panelist. Saltine crackers were provided along with water for wash out between test solutions. Each panelist rated each of the solutions according to sweetness (in Brix) and sourness (yes or no). The intensity of each attribute was also collected.

Results

Table 2 and Table 3 show the results of the comparative tests. The results are depicted as the average of the results from all the panelists.

TABLE 2

| Sucrose Sucrose | |
|---|---|
| ×1000 PPM | Brix (average) |
| 10 (1%) | 1.3 |
| 20 (2%) | 2.6 |
| 30 (3%) | 3.4 |
| 40 (4%) | 5.2 |

TABLE 3

| Reb-E Reb-E | |
|---|---|
| PPM | Brix (average) |
| 20 | 1.2 |
| 40 | 2.1 |
| 50 | 2.2 |
| 60 | 2.6 |

The sweetness of Reb-E and sucrose as a function of concentration was also determined (FIG. 1). The results show a near linear correlation between Reb-E sweetness and concentration.

The ability of Reb-E to overcome sourness was also measured, and compared to sucrose. Panelists were asked to detect the presence of sourness by a yes or no rating. The results are shown in Table 4 and Table 5.

TABLE 4

| Sucrose Sucrose | | |
|---|---|---|
| ×1000 PPM | Yes | No |
| 10 (1%) | 8 | 4 |
| 20 (2%) | 4 | 2 |
| 30 (3%) | 1 | 5 |
| 40 (4%) | 4 | 2 |

TABLE 5

| Reb-E Reb-E | | |
|---|---|---|
| PPM | Yes | No |
| 20 | 10 | 2 |
| 40 | 4 | 2 |
| 50 | 11 | 1 |
| 60 | 6 | 0 |

The results demonstrate that the sweetness of Reb-E at a range from 20 ppm to 60 ppm is equivalent to the sweetness of a sucrose solution at concentration that ranges from 1% to 3% (i.e., (10,000 to 30,000 ppm). The sourness tests indicated that Reb-E was not as effective in covering the sourness as compared to sucrose solutions within the tested range.

What is claimed is:

1. An orally consumable product comprising rebaudioside E present in about 5 ppm to about 100 ppm, and further comprising rebaudioside D, wherein the orally consumable product has a sweetness intensity provided by the rebaudioside E and rebaudioside D, that is equivalent to the sweetness intensity of a solution comprising about 1% to about 8% (w/v-%) sucrose or about 10,000 ppm to about 80,000 ppm sucrose, wherein the orally consumable product is selected from the group consisting of a foodstuff composition, a beverage product, a dietary supplement, a nutraceutical, an edible gel mix, an edible gel composition, a pharmaceutical composition, a dental composition, and an oral hygiene composition.

2. The orally consumable product of claim 1, wherein rebaudioside E is present in about 20 ppm to about 100 ppm.

3. The orally consumable product of claim 1, wherein rebaudioside E is present in about 5 ppm to about 60 ppm.

4. The orally consumable product of claim 1, wherein rebaudioside E is present in about 20 ppm to about 60 ppm.

5. The orally consumable product of claim 1, wherein the rebaudioside E in the orally consumable product is a rebaudioside E polymorph or amorphous rebaudioside E.

6. The orally consumable product of claim 1, wherein the rebaudioside E in the orally consumable product is a rebaudioside E stereoisomer.

7. The orally consumable product of claim 1, wherein the orally consumable product is a foodstuff composition selected from the group consisting of a confectionary composition, a condiment, a chewing gum, a cereal composition, a baked good, a dairy product, and a tabletop sweetener composition.

8. The orally consumable product of claim 1, wherein the orally consumable product is a carbonated or non-carbonated beverage product.

9. The orally consumable product claim 1, wherein the orally consumable product is a beverage product selected from the group consisting of a soft drink, a fountain beverage, a frozen and ready-to-drink beverage, coffee, tea, a dairy beverage, a powdered soft drink, a liquid concentrate, flavored water, enhanced water, fruit juice, a fruit juice flavored drink, a sport drink, and an energy drink.

10. The orally consumable product of claim 1, wherein the orally consumable product has a sweetness intensity equivalent to the sweetness intensity of a solution comprising about 1% to about 6% (w/v-%) sucrose.

11. The orally consumable product of claim 10, wherein the orally consumable product has a sweetness intensity equivalent to the sweetness intensity of a solution comprising about 1% to about 4% (w/v-%) sucrose.

12. The orally consumable product of claim 1, wherein rebaudioside E is present in about 20 ppm to about 60 ppm, and wherein the orally consumable product has a sweetness intensity provided by the rebaudioside E and rebaudioside D that is equivalent to the sweetness intensity of a solution comprising about 1% to about 3% (w/v-%) sucrose or about 10,000 ppm to about 30,000 ppm sucrose.

13. The orally consumable product of claim 1, wherein the rebaudioside E provides about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, or about 95% of the total sweetening of the orally consumable product.

* * * * *